United States Patent
Wang et al.

(10) Patent No.: US 9,412,369 B2
(45) Date of Patent: Aug. 9, 2016

(54) AUTOMATED ADVERSE DRUG EVENT ALERTS

(75) Inventors: Tao Wang, Beijing (CN); Bin Zhou, Beijing (CN)

(73) Assignee: Microsoft Technology Licensing, LLC, Redmond, WA (US)

( * ) Notice: Subject to any disclaimer, the term of this patent is extended or adjusted under 35 U.S.C. 154(b) by 1069 days.

(21) Appl. No.: 13/162,585

(22) Filed: Jun. 17, 2011

(65) Prior Publication Data

US 2012/0323576 A1    Dec. 20, 2012

(51) Int. Cl.
*G10L 15/26* (2006.01)

(52) U.S. Cl.
CPC ........................ *G10L 15/26* (2013.01)

(58) Field of Classification Search
CPC ......... G10L 15/22; G10L 15/24; G10L 15/26; G10L 15/28; G10L 15/285
USPC .............................................. 704/236, 270.1
See application file for complete search history.

(56) References Cited

U.S. PATENT DOCUMENTS

| | | | |
|---|---|---|---|
| 5,940,793 A * | 8/1999 | Attwater et al. | 704/231 |
| 6,014,631 A | 1/2000 | Teagarden et al. | |
| 6,161,087 A * | 12/2000 | Wightman et al. | 704/215 |
| 6,182,029 B1 * | 1/2001 | Friedman | 704/9 |
| 6,748,353 B1 * | 6/2004 | Iliff | 704/9 |
| 2002/0016736 A1 * | 2/2002 | Cannon et al. | 705/14 |
| 2002/0055845 A1 * | 5/2002 | Ueda et al. | 704/270 |
| 2004/0024617 A1 * | 2/2004 | Fralic | 705/2 |
| 2004/0267527 A1 * | 12/2004 | Creamer et al. | 704/235 |
| 2005/0114283 A1 * | 5/2005 | Pearson et al. | 706/50 |
| 2005/0165598 A1 * | 7/2005 | Cote et al. | 704/1 |
| 2005/0278165 A1 * | 12/2005 | Boillot et al. | 704/200.1 |
| 2006/0041428 A1 | 2/2006 | Fritsch et al. | |
| 2007/0265838 A1 * | 11/2007 | Chopra et al. | 704/201 |
| 2008/0081956 A1 * | 4/2008 | Shah et al. | 600/300 |
| 2009/0187425 A1 * | 7/2009 | Thompson | 705/3 |
| 2010/0088095 A1 | 4/2010 | John | |
| 2011/0098544 A1 * | 4/2011 | Shah et al. | 600/323 |

(Continued)

OTHER PUBLICATIONS

Shapiro, Lynn., "Pharmacy Technology", Retrieved Jun. 17, 2011 at 21 <http://drugtopics.modernmedicine.com/drugtopics/Modern+Medicine+Now/Pharmacy-technology-2010/ArticleStandard/Article/detail/681905 >>, Aug. 15, 2010, 5 Pages.

(Continued)

*Primary Examiner* — Eric Yen
(74) *Attorney, Agent, or Firm* — Sandy Swain; Micky Minhas

(57) ABSTRACT

Event audio data that is based on verbal utterances associated with a pharmaceutical event associated with a patient may be received. Medical history information associated with the patient may be obtained, based on information included in a medical history repository. At least one text string that matches at least one interpretation of the event audio data may be obtained, based on information included in a pharmaceutical speech repository, information included in a speech accent repository, and a drug matching function, the at least one text string being associated with a pharmaceutical drug. One or more adverse drug event (ADE) alerts may be determined based on matching the at least one text string and medical history attributes associated with the at least one patient with ADE attributes obtained from an ADE repository. An ADE alert report may be generated, based on the determined one or more ADE alerts.

20 Claims, 9 Drawing Sheets

(56) References Cited

U.S. PATENT DOCUMENTS

2012/0212337 A1* 8/2012 Montyne et al. .............. 340/501
2012/0215532 A1* 8/2012 Foo et al. ..................... 704/235

OTHER PUBLICATIONS

Spenceley, et al., "The Intelligent Interface for on-Line Electronic Medical Records using Temporal Data Mining", Retrieved Feb. 25, 2011 at <<http://ieeexplore.ieee.org/stamp/stamp.jsp?tp=&arnumber=648321>>, Thirty-First Annual Hawaii International Conference on System Sciences, vol. 5, 1998, 9 Pages.

Ferguson, et al., "The Medication Advisor Project: Preliminary Report", Retrieved Feb. 25, 2011 at <<http://citeseerx.ist.psu.edu/viewdoc/download?doi=10.1.1.19.5511&rep=rep1&type=pdf>>, Technical Report 776, May 2002, 34 Pages.

Nemeth, et al., "Speech based Drug Information System for Aged and Visually Impaired Persons", Retrieved Feb. 25, 2011 at <<http://mycite.omikk.bme.hu/doc/12444.pdf>>, INTERSPEECH 2007, pp. 2533-2536.

"Cost-Effective Patient Retention Improvements", Retrieved Feb. 25, 2011 at <<http://www.voiceport.net/PpHome.php>>, 1 Page.

"An Introductory Guide to Speech Recognition Solutions," Retrieved Jun. 16, 2011 at <<ftp://ftp.comptek.ru/pub/Envox/EvaluationSoftware/CD2/Autorun/pages/samples/White%20Papers/An%20Introductory%20Guide%20to%20Speech%20Recognition%20Solutions%20v%202.pdf>>, DATAMONITOR, 2006, 20 pages.

Cooper, Charles "The Future of Talking Computers," Retrieved Jun. 16, 2011 at <<http://news.cnet.com/2008-1011_3-5090381.html?tag=st_rn>>, CNET News, Oct. 13, 2003, 2 Pages.

Sharma, Dinesh C., "Microsoft Handhelds Find Their Voice," Retrieved Jun. 16, 2011 at <<http://news.com.com/2100-1046-5101193.html>>, CNET News, Nov. 3, 2003, 1 Page.

Eisenberg, Anne, "What's Next; Is That You, Son? Voice Authentication Trips Up the Experts," Retrieved Jun. 16, 2011 at <<http://www.nytimes.com/2003/11/13/technology/circuits/13next.html?adxnnl=1&adxnnlx=1069285421-l1EJE+7wZPy0+t79yv0xjw>>, The New York Times, Nov. 13, 2003, 2 Pages.

McEvoy, Aoife, "Dragon: Worth Talking To," Retrieved Jun. 16, 2011 at <<http://www.businessweek.com/technology/content/jan2002/tc20020130_6540.htm>>, PC World Product Review, Jan. 30, 2002, 1 Page.

Matthews, James, "How Does Speech Recognition Work?", Retrieved Jun. 17, 2011 at <<http://www.generation5.org/content/2002/howsrworks.asp?Print=1>>, generation5, 2002, 3 Pages.

"Adverse Event Reporting System (AERS)," Retrieved Jun. 16, 2011 at <<http://www.fda.gov/Drugs/GuidanceComplianceRegulatoryInformation/Surveillance/AdverseDrugEffects/default.htm>>, FDA, 2009, 2 Pages.

"MedWatch: The FDA Safety Information and Adverse Event Reporting Program," Retrieved Jun. 16, 2011 at <<http://www.fda.gov/Safety/MedWatch/default.htm>>, FDA, Jun. 16, 2011, 2 Pages.

"Index to Drug-Specific Information," Retrieved Jun. 17, 2011 at <<http://www.fda.gov/Drugs/DrugSafety/PostmarketDrugSafetyInformationforPatientsandProviders/ucm111085.htm>>, FDA, Jun. 13, 2011, 22 Pages.

"FDA Approved Drug Products," Retrieved Jun. 17, 2011 at <<http://www.accessdata.fda.gov/scripts/cder/drugsatfda/index.cfm>>, FDA, Jun. 16, 2011, 1 Page.

\* cited by examiner

400b (4A)
↓

┌─────────────────────────────────────────────────────────────┐
│ Initiate the graphical output depicting a population of at least one field of the │
│ electronic pharmaceutical form, based on one or more of: │
│ initiating a graphical display of the populated electronic pharmaceutical form │
│ on a display device, based on the first plurality of strings of text alert │ 414
│ information from the ADE alert repository, the ADE alert report form, and the │
│ received template information, initiating a graphical output to a printer, based │
│ on the first plurality of strings of text alert information from the ADE alert │
│ repository, the ADE alert report form, and the received template information, │
│ or initiating a graphical output to an electronic file, based on the first plurality │
│ of strings of text alert information from the ADE alert repository, the ADE alert │
│ report form, and the received template information │
└─────────────────────────────────────────────────────────────┘

(4C)
↓

┌─────────────────────────────────────────────────────────────┐
│ Initiate the communication of the audio alert to the audio output device │
│ associated with the user, based on one or more of: │ 416
│ initiating a text-to-speech conversion of the text alert information based on │
│ the audio alert to the audio output device associated with the user, or │
│ initiating an audio output of at least one recorded audio alert obtained from an │
│ ADE alert repository │
└─────────────────────────────────────────────────────────────┘

Patient Name: John Doe — 602

Date of Visit: February 26, 2011 — 604

D.O.B.: March 12, 1975

Patient ID: 143567

Attending Physician: Dr. Watson — 608

History:
Mother and father allergies to penicillin
Patient past adverse reaction to penicillin — 610

Submitted Prescription:
Depen 500mg capsule, 4xdaily — 606

ALERT: PATIENT MAY BE ALLERGIC TO PENICILLIN – CAUTION REGARDING DEPEN USAGE!!!!! — 612

PATIENT ADVERSE DRUG EVENT ALERT REPORT — 614

FIG. 6

AUTOMATED ADVERSE DRUG EVENT ALERTS

BACKGROUND

In pharmaceutical environments, a patient may need to fill one or more prescriptions provided to them by one or more physicians. For example, a patient recovering from injuries sustained in an automobile accident may be receiving medical treatment from several medical specialists, including neurologists, internal medicine specialists, ophthalmologists, orthopedists, and dentists. Each specialist may prescribe various medications to help the patient in the recovery process, including pain medications, antibiotics, and/or eye drops. Further, medical personnel may discover that the patient is overdue for immunizations such as tetanus shots or H1N1 shots.

Physicians may ask the patient questions, and may manually scan the patient's medical record to try to determine whether the patient may have any allergies or past history of adverse reactions to certain drugs. The physicians may also try to determine whether there is any family history that might indicate whether any biological relatives of the patient have experienced allergies, reactions, or other conditions that might provide reasons for the current patient to avoid certain drugs. Further, the physicians may try to determine whether the patient has been consuming other drugs or substances that may interact unfavorably with potential newly prescribed drugs or substances.

SUMMARY

According to one general aspect, a pharmaceutical alert speech engine may include a medical history interface engine configured to access a medical history repository that includes medical history information associated with a plurality of patients. The pharmaceutical alert speech engine may also include an audio data receiving engine configured to receive event audio data that is based on verbal utterances associated with a pharmaceutical event associated with at least one of the patients. The pharmaceutical alert speech engine may also include a recognition engine configured to obtain at least one text string that matches at least one interpretation of the received event audio data, based on information obtained from a pharmaceutical speech repository, information obtained from a speech accent repository, and a drug matching function, the at least one text string associated with a pharmaceutical drug. The pharmaceutical alert speech engine may also include a record retrieval engine configured to obtain medical history information associated with the at least one of the patients. The pharmaceutical alert speech engine may also include an adverse drug event (ADE) scanning engine configured to determine, via an alert device processor, one or more adverse drug event alerts based on matching the at least one text string and medical history attributes associated with the at least one of the patients with ADE attributes obtained from an ADE repository. The pharmaceutical alert speech engine may also include an audio data output interface engine configured to initiate a transmission of an audio alert associated with the one or more ADE alerts to an audio output device.

According to another aspect, a computer program product tangibly embodied on a computer-readable medium may include executable code that, when executed, is configured to cause at least one data processing apparatus to receive event audio data that is based on verbal utterances associated with a pharmaceutical event associated with a patient, and obtain medical history information associated with the patient, based on information included in a medical history repository. Further, the data processing apparatus may obtain at least one text string that matches at least one interpretation of the event audio data, based on information included in a pharmaceutical speech repository, information included in a speech accent repository, and a drug matching function, the at least one text string associated with a pharmaceutical drug. Further, the data processing apparatus may determine one or more adverse drug event (ADE) alerts based on matching the at least one text string and medical history attributes associated with the at least one patient with ADE attributes obtained from an ADE repository, and may generate an ADE alert report, based on the determined one or more ADE alerts.

According to another aspect, a computer program product tangibly embodied on a computer-readable medium may include executable code that, when executed, is configured to cause at least one data processing apparatus to receive an indication of a receipt of event audio data from a user that is based on verbal utterances associated with a pharmaceutical event associated with a patient, and receive an indication of an ADE alert report based on a first plurality of strings of text alert information from an ADE alert repository and an ADE alert report form. Further, the data processing apparatus may receive an indication of an audio alert based on a second plurality of strings of text alert information from the ADE alert repository, and initiate communication of the audio alert to an audio output device associated with the user. Further, the data processing apparatus may receive template information associated with an electronic pharmaceutical form, and initiate a graphical output depicting a population of at least one field of the electronic pharmaceutical form, based on the first plurality of strings of text alert information from the ADE alert repository, the ADE alert report form, and the received template information.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. The details of one or more implementations are set forth in the accompanying drawings and the description below. Other features will be apparent from the description and drawings, and from the claims.

DRAWINGS

FIGS. 4a-4b are a flowchart illustrating example operations of the system of FIG. 1.

FIG. 6 depicts an example graphical view of a populated adverse drug event alert report.

DETAILED DESCRIPTION

Figure 1:
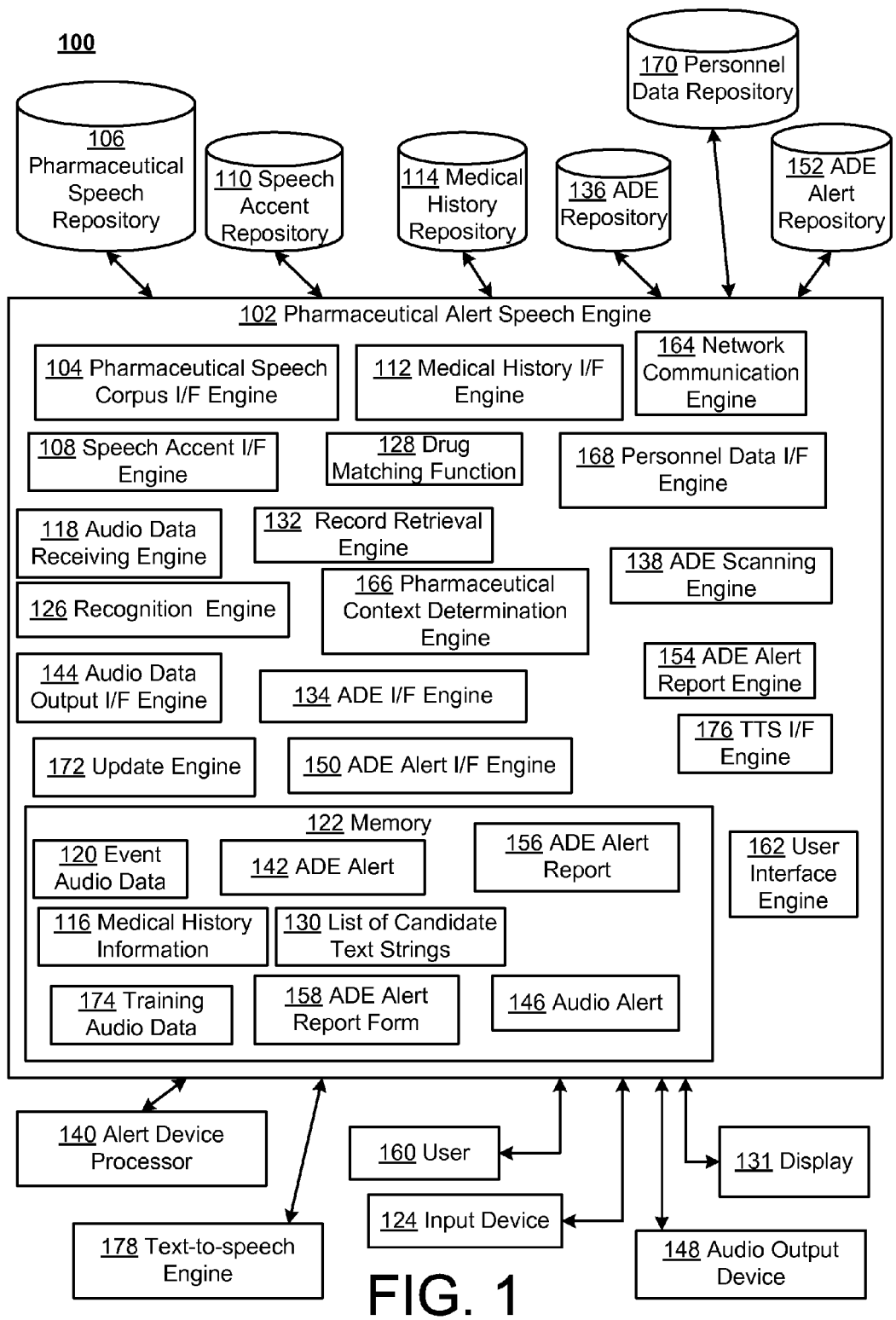
FIG. 1 is a block diagram of an example system for automated adverse drug event alerts.

In a pharmaceutical environment, a patient or caretaker may present one or more prescription forms to a pharmacist, requesting that the pharmacist provide the prescribed drugs or other items for use or consumption by the patient. The patient or caretaker may also request that the pharmacist query an electronic medical care system to ascertain prescriptions that may have been entered into the system and authorized/authenticated by one or more physicians so that the patient may receive their medications at the pharmacy when available.

If the patient has consulted with multiple physicians or medical specialists, he/she may have multiple sources of the prescriptions. However, if the patient has received prescriptions from several physicians in a short time frame, one or more of the physicians may have been unable to ascertain everything that the patient would ultimately be receiving at the pharmacy (e.g., prescriptions from other physicians may not yet have appeared in the system). Additionally, adverse drug events may be reported to various local and national systems as they are discovered, and the physicians and/or pharmacists may not yet be aware of recent warnings with respect to a combination of drugs or a combination of a particular drug and other factors that may pertain to this patient (e.g., allergies, family history).

As another example, a physician may need to request drugs or other pharmaceutical items for a patient while engaged in treatment of the patient, or other activities. For example, a surgeon may be using both hands for surgery, and may dynamically determine a need for a particular drug to be sent from a hospital pharmacy, on an immediate basis. The surgeon may thus not have an ability to spend time accessing the patient's medical history to determine whether there may exist a risk of adverse drug effects from the surgeon's emergency administration of a particular drug during the surgery.

Example techniques discussed herein may provide pharmaceutical personnel such as pharmacists, pharmaceutical technicians, and physicians with example systems that may accept verbal input to determine whether particular drugs or other pharmaceutical items may initiate adverse effects for the patient. Thus, a pharmacist, pharmaceutical technician, or physician treating or otherwise meeting with a patient may speak drug and prescription information, and an example speech-to-text conversion may quickly provide audio and/or textual information for alerting the patient, caretaker, physician, or pharmacist to potential adverse drug events (ADEs) that may be associated with the patient's use of the prescribed drugs or other items, as discussed further below. Since many pharmaceutical terms may have similar sounds in pronunciation (e.g., based on phonemes), or may have closely related, but different, meanings, a matching function may be applied to provide one or more text strings for review or for comparison with patient history information and information obtained from a database that includes ADE information associated with particular drugs.

As further discussed herein, FIG. 1 is a block diagram of a system 100 for automated adverse drug event alerts. As shown in FIG. 1, a system 100 may include a pharmaceutical alert speech engine 102 that includes a pharmaceutical speech corpus interface engine 104 that may be configured to access a pharmaceutical speech repository 106 that includes information associated with a corpus of pharmaceutical terms.

For example, the pharmaceutical speech repository 106 may include text strings associated with standard pharmaceutical terms, as well as text strings that may be used in a localized environment such as a medical care center or chain (e.g., a hospital, a private office of a physician, a privately owned pharmacy). The pharmaceutical speech repository 106 may also include information associating various audio data with the pharmaceutical terms, including information regarding terms that may have similar pronunciations, as well as terms that may have different pronunciations, but similar meanings. For example, in a particular context, a particular term may be meaningful, but another term that has a different pronunciation may provide a meaning with better clarity for a given situation, in a pharmaceutical environment.

According to an example embodiment, the pharmaceutical speech repository 106 may include text strings associated with pharmaceutical terms that include a name attribute associated with the pharmaceutical drug (e.g., aspirin, penicillin), a strength attribute associated with the pharmaceutical drug (e.g., 25 mg, 300 ml, 50 mg caplet), or a dosage attribute associated with the pharmaceutical drug (e.g., 3×daily, take 2 hours before or after meals).

A speech accent interface engine 108 may be configured to access a speech accent repository 110 that includes information associated with database objects indicating speech accent attributes associated with one or more speakers. For example, a speaker may speak with a dialect associated with a distinct region or province of a country (e.g., with a "Boston accent" or a "Texas drawl"). Further, each individual speaker may have personal speech attributes associated with their individual speech patterns, which may be discernable via voice recognition techniques. For example, a user of the system 100 may provide a training sample of his/her voice speaking various predetermined terms so that audio attributes of that user's speech may be stored in the speech accent repository 110 for use in matching audio data with terms in the pharmaceutical speech repository 106 (e.g., via speech recognition). According to an example embodiment, the information stored in the speech accent repository 110 may also be used to determine an identification of a user (e.g., via voice recognition). According to an example embodiment, the information stored in the speech accent repository 110 may include speech accent information that is not personalized to particular users.

A medical history interface engine 112 may be configured to access a medical history repository 114 that includes medical history information 116 associated with a plurality of patients. According to an example embodiment, the medical history information 116 associated with the at least one of the patients may include one or more of a consumption history associated with the at least one of the patients, an allergy history associated with the at least one of the patients, an allergy history associated with at least one family member biologically related to the at least one of the patients, a medical condition associated with the at least one of the patients, or a medical condition associated with at least one family member biologically related to the at least one of the patients. For example, the consumption history may include a history of consumption of various drugs, vitamins, foods, drinks, or supplements by the patient.

For example, the medical history repository 114 may include names associated with medical diagnoses for each patient (e.g., myocardial infarction, stress fracture), names of body parts (e.g., tibia, clavicle), names of patient complaints (e.g., fever, temperature measurements, nausea, dizziness), names of observations (e.g., contusion, confusion, obese, alert), names of inoculations or shots (e.g., tetanus, smallpox, flu), names of tests and results (e.g., blood pressure, pulse, weight, temperature, cholesterol numbers, blood sample), names of diseases (e.g., chicken pox, measles), names associated with patient histories (e.g., family history of cancer, non-smoker, social drinker, three pregnancies, family history of deaths associated with blood thinners), and allergy information (e.g., allergy to penicillin).

According to an example embodiment, the medical history repository 114 may include a plurality of electronic medical records associated with the plurality of patients.

An audio data receiving engine 118 may be configured to receive event audio data 120 that is based on verbal utterances associated with a pharmaceutical event associated with at least one of the patients. According to an example embodiment, a memory 122 may be configured to store the event audio data 120. In this context, a "memory" may include a single memory device or multiple memory devices configured to store data and/or instructions. Further, the memory 122 may span multiple distributed storage devices.

For example, a pharmacist or other pharmaceutical or medical personnel may speak in range of an input device 124 that may include an audio input device, regarding the pharmaceutical event.

According to an example embodiment, the pharmaceutical event may include one or more of a medical prescription receiving event associated with the at least one patient, or a medical prescription review event associated with the at least one of the patients.

Thus, for example, a physician may be examining an in-patient in a hospital room, and may be speaking pharmaceutical information while he/she is with the patient. Thus, it may be possible to provide a verbal input to the input device 124 at the same time as providing verbal information to the patient or to caregivers of the patient. For example, a pharmacist may speak the drug information into the input device 124 while speaking with the patient or caregiver at a pharmacy counter.

For example, the input device 124 may include a mobile audio input device that may be carried with the physician/pharmacist as he/she navigates from one patient or medical/pharmaceutical event to the next. For example, the event audio data 120 may be transmitted via a wired or wireless connection to the pharmaceutical alert speech engine 102. The input device 124 may also include one or more audio input devices (e.g., microphones) that may be located in pharmacies, the operating rooms, emergency rooms, patient rooms, or in the hallways outside the patient rooms, or in offices provided for medical personnel and/or pharmaceutical personnel.

A recognition engine 126 may be configured to obtain at least one text string that matches at least one interpretation of the received event audio data 120, based on information received from the pharmaceutical speech corpus interface engine 104, information received from the speech accent interface engine 108, and a drug matching function 128, the at least one text string associated with a pharmaceutical drug.

According to an example embodiment, the drug matching function 128 may include one or more of a phoneme matching function configured to determine the at least one text string based on at least one phoneme, a user history matching function configured to determine the at least one text string based on a history of selected text strings associated with a user, or a patient history matching function configured to determine the at least one text string based on a history of selected text strings associated with the patient.

According to an example embodiment, the drug matching function 128 may include one or more of a name matching function configured to determine the at least one text string based on a name associated with the pharmaceutical drug, or an alternative drug matching function configured to determine the at least one text string based on a name associated with an alternative drug associated with the pharmaceutical drug. For example, the alternative drug may include a generic or name brand equivalent of a drug.

According to an example embodiment, the at least one text string may include one or more of a name attribute associated with the pharmaceutical drug, a strength attribute associated with the pharmaceutical drug, or a dosage attribute associated with the pharmaceutical drug.

According to an example embodiment, the recognition engine 126 may obtain a list of a plurality of candidate text strings 130 that match interpretations of the received event audio data 120, based on information received from the pharmaceutical speech corpus interface engine 104, information received from the speech accent interface engine 108, and the drug matching function 128. For example, the drug matching function 128 may include a fuzzy matching technique which may provide suggestions of text strings that approximately match portions of the event audio data 120, based on information included in the pharmaceutical speech repository 106 and the speech accent repository 110. According to an example embodiment, the suggestions may be presented to the user for obtaining a selection of a most relevant text string. According to an example embodiment, the user may provide revisions to a suggested text string.

According to an example embodiment, the suggestions may be provided to the user via an audio output device. According to an example embodiment, the suggestions may be provided to the user via a graphical display or print version. For example, the graphical display may be transmitted to a display device 131.

According to an example embodiment, a user selection or revision may be received via audio input. According to an example embodiment, the user selection or revision may be received via the input device 124 (e.g., a keyboard, keypad, touchscreen device, video data receiving device, or other manual, sensing, or tactile input devices).

According to an example embodiment, a speech recognition technique may include extracting phonemes from the event audio data 120. For example, phonemes may be formally described as linguistic units, or as sounds that may be aggregated by humans in forming spoken words. For example, a human conversion of a phoneme into sound in speech may be based on factors such as surrounding phonemes, an accent of the speaker, and an age of the speaker. For example, a phoneme of "uh" may be associated with the "oo" pronunciation for the word "book" while a phoneme of "uw" may be associated with the "oo" pronunciation for the word "too."

For example, the phonemes may be extracted from the event audio data 120 via an example extraction technique based on at least one Fourier transform (e.g., if the event audio data 120 is stored in the memory 122 based on at least one representation of waveform data). For example, a Fourier transform may include an example mathematical operation that may be used to decompose a signal (e.g., an audio signal generated via an audio input device) into its constituent frequencies.

For example, the extracted phonemes may be arranged in sequence (e.g., the sequence as spoken by the speaker of the event audio data 120), and a statistical analysis may be performed based on at least one Markov model, which may include at least one sequential path of phonemes associated with spoken words, phrases, or sentences associated with a particular natural language.

One skilled in the art of data processing may appreciate that there are many techniques available for translating voice to text and for speech recognition, and that variations of these techniques may also be used, without departing from the spirit of the discussion herein.

A record retrieval engine 132 may be configured to obtain medical history information 116 associated with the at least one of the patients via the medical history interface engine 112.

According to an example embodiment, an adverse drug event (ADE) interface engine 134 may be configured to access an ADE repository 136 that includes attributes associated with adverse drug events. For example, the ADE repository 136 may include a local database, or it may include a worldwide or national database that accepts ADE information from subscriber medical/pharmaceutical personnel. For example, the United States Food and Drug Administration (FDA) may host a database of FDA approved drugs that includes attributes associated with drugs such as drug names, equivalent drugs, dosages and strengths, manufacturer names, and ADE information associated with the drugs. For example, the ADE repository 136 may be accessible to the pharmaceutical alert speech engine 102 via a network such as the Internet.

An adverse drug event (ADE) scanning engine 138 may be configured to determine, via an alert device processor 140, one or more adverse drug event alerts 142 based on matching the at least one text string and medical history attributes associated with the at least one of the patients with ADE attributes obtained from the ADE interface engine 134.

In this context, a "processor" may include a single processor or multiple processors configured to process instructions associated with a processing system. A processor may thus include multiple processors processing instructions in parallel and/or in a distributed manner.

An audio data output interface engine 144 may be configured to initiate a transmission of an audio alert 146 associated with the one or more ADE alerts 142 to an audio output device 148.

According to an example embodiment, an ADE alert interface engine 150 may be configured to access an ADE alert repository 152 configured to store information associated with a plurality of ADE alerts 142, the ADE alerts 142 including one or more of a plurality of recorded audio alerts each associated with a predetermined ADE alert, a plurality of textual alerts, each textual alert associated with a predetermined ADE alert, or a plurality of alert text strings, each alert text string associated with a predetermined attribute associated with a predetermined adverse condition. For example, a textual alert "possible allergy to penicillin" may be stored in the ADE alert repository 152.

According to an example embodiment, the recognition engine 126 may be configured to obtain the at least one text string that matches the at least one interpretation of the received event audio data 120, based on information obtained from the pharmaceutical speech corpus interface engine 104, information received from the speech accent interface engine 108, and the drug matching function 128.

According to an example embodiment, the record retrieval engine 126 may be configured to obtain the medical history information 116 associated with the at least one of the patients via the medical history interface engine 112.

According to an example embodiment, the adverse drug event (ADE) scanning engine 138 may be configured to determine the one or more adverse drug event alerts 142 based on matching the at least one text string and the medical history attributes associated with the at least one of the patients with ADE attributes obtained via the ADE interface engine 134.

According to an example embodiment, an ADE alert report engine 154 may be configured to generate an ADE alert report 156 based on obtaining one or more strings of text alert information via the ADE alert interface engine 150 and populating one or more fields associated with an ADE alert report form 158.

According to an example embodiment, the audio data output interface engine 144 may be configured to initiate the transmission of the audio alert 146 based on obtaining one or more strings of text alert information via the ADE alert interface engine 150 and initiating a text-to-speech transmission of the text alert information via the audio alert 146 to the audio output device 148.

According to an example embodiment, the drug matching function 128 may include a matching function configured to determine a first candidate text string and at least one fuzzy derivative candidate text string, a matching function configured to determine the plurality of candidate text strings based on at least one phoneme, a matching function configured to determine the plurality of candidate text strings based on a history of selected text strings associated with a user 160, or a matching function configured to determine the plurality of candidate text strings based on a history of selected text strings associated with the patient.

For example, the drug matching function 128 may include a fuzzy matching algorithm configured to determine a plurality of candidate text strings 130 that are approximate textual matches as transcriptions of portions of the event audio data 120. For example, the fuzzy matching algorithm may determine that a group of text strings are all within a predetermined threshold value of "closeness" to an exact match based on comparisons against the information in the pharmaceutical speech repository 106 and the speech accent repository 110. The candidate text strings 130 may then be "proposed" to the user 160, who may then accept a proposal or edit a proposal to more fully equate with the intent of the user 160 in his/her speech input. In this way, fuzzy matching may expedite the transcription process and provide increased productivity for the user 160.

According to an example embodiment, a user interface engine 162 may be configured to manage communications between the user 160 and the pharmaceutical alert speech engine 102. A network communication engine 164 may be configured to manage network communication between the pharmaceutical alert speech engine 102 and other entities that may communicate with the pharmaceutical alert speech engine 102 via one or more networks.

For example, the ADE alert report form 158 may include fields for a name of the patient, a name of an attending physician, a date of the patient event, a patient identifier, a summary of patient complaints and observable medical attributes, a patient history, a diagnosis summary, and an indication of a prescribed drug or an indication of an ADE alert 142. For example, form template information may be provided in a structured format such as HyperText Markup Language (HTML) or Extensible Markup Language (XML) format, and may provide labels for each field for display to the user. For example, the template information may be stored in a local machine or a server such as a Structured Query Language (SQL) server.

According to an example embodiment, a pharmaceutical context determination engine 166 may be configured to determine a pharmaceutical context based on the received event audio data 120. For example, the user 160 may speak words that are frequently used in a context of prescribing a prescription medication (e.g., a name and dosage of a prescription medication), and the pharmaceutical context determination engine 166 may determine that the context is a prescription context.

According to an example embodiment, the user interface engine 162 may be configured to obtain an identification of the user 160. For example, the user 160 may speak identifying information such as his/her name, employee identification number, or other identifying information. For example, the user 160 may swipe or scan an identification card via a swiping or scanning input device included in the input device 124.

For example, the user 160 may provide a fingerprint for identification via a fingerprint input device included in the input device 124.

According to an example embodiment, a personnel data interface engine 168 may be configured to access a personnel data repository 170 that may be configured to store information associated with personnel associated with the medical/pharmaceutical facility associated with the system 100. For example, the personnel data repository 170 may store identifying information associated with physicians, nurses, administrative personnel, and pharmaceutical technicians. For example, the identifying information may include a name, an employee number or identifier, voice recognition information, fingerprint recognition information, and authorization levels. For example, a physician/pharmacist may be authorized to provide and update patient prescription information associated with narcotic drugs, while administrative personnel may be blocked from entry of prescription information. Thus, for example, non-physician/non-pharmaceutical administrative personnel may not be allowed to access patient history information from the medical history repository 114.

According to an example embodiment, medical personnel or a patient may be identified based on input information and information obtained from the personnel data repository 170 or the medical history repository 114, and corresponding fields of the ADE alert report form 158 may be populated based on the identifying information. For example, if the user 160 is identified by voice recognition, then the name of the user 160 may be filled in for a physician/pharmacist name in the ADE alert report form 158.

According to an example embodiment, the recognition engine 126 may be configured to obtain the list 130 based on information included in the pharmaceutical speech repository 106, information that is associated with the user 160 and is included in the speech accent repository 110, and the drug matching function 128. For example, the user 160 may develop a history of selecting particular text strings based on particular speech input, and the speech accent repository 110 may be updated to reflect the particular user's historical selections. Thus, the speech accent repository 110 may be trained over time to provide better matches for future requests from individual users 160.

According to an example embodiment, the user interface engine 162 may be configured to obtain an identification of the user 160, based on receiving an indication of the identification from the user 160 or obtaining the identification based on matching a portion of the event audio data 120 with a portion of the information included in the speech accent repository 110, based on voice recognition.

According to an example embodiment, the verbal utterances may be associated with a physician or pharmacist designated as a physician or pharmacist responsible for treatment of the patient.

According to an example embodiment, the recognition engine 126 may be configured to obtain the list 130 based on obtaining the list of the plurality of candidate text strings that match interpretations of the event audio data 120, based on information included in the pharmaceutical speech repository 106 that includes information associated with a vocabulary that is associated with pharmaceutical professional terminology and a vocabulary that is associated with a predetermined pharmaceutical environment. For example, the pharmaceutical speech repository 106 may include information associated with pharmaceutical professionals worldwide, as well as localized information associated with pharmaceutical personnel locally (e.g., within the environment of the medical/pharmaceutical facility). For example, personnel local to a particular medical/pharmaceutical facility may use names and descriptions that develop over time in a local community, and that may not be globally recognized.

According to an example embodiment, the user interface engine 162 may be configured to receive at least one revision to a selected text string, based on input from the user 160. For example, the user 160 may be provided the list 130, and may decide to revise at least one of the candidate text strings for better clarity.

According to an example embodiment, an update engine 172 may be configured to receive training audio data 174 that is based on verbal training utterances associated with the user 160, and initiate an update event associated with the speech accent repository 110 based on the received training audio data 174. For example, the user 160 may provide training audio input that may include audio data of the user 160 reading prescription data, for training the speech accent repository 110 to better match event audio data 120 obtained from the user 160 with information included in the pharmaceutical speech repository 106.

According to an example embodiment, the update engine 172 may be configured to initiate an update event associated with the speech accent repository 110 based on an obtained selection. For example, the speech accent repository 110 may receive training information associated with the user 160 over time, based on a history of text string selections that are based on the received event audio data 120.

According to an example embodiment, a text-to-speech interface engine 176 may be configured to access a text-to-speech engine 178 that may be configured to obtain audio output data based on text string input data. According to an example embodiment, the text-to-speech engine 178 may be configured to obtain audio output data based on text string input data combined with audio data. For example, the text-to-speech engine 178 may obtain audio output data based on the ADE alert report 156. For example, the text-to-speech engine 178 may obtain audio output data based on the text strings associated with ADE alerts and one or more audio alerts 146.

For example, the text-to-speech engine 178 may convert raw text that includes symbols such as numbers and abbreviations into an equivalent of non-abbreviated words (e.g., text normalization, pre-processing, tokenization). Phonetic transcriptions may then be associated with each word, and the text may be divided and marked into prosodic units (e.g., phrases, clauses, and sentences). For example, phonetic transcriptions may be assigned to words (e.g., via text-to-phoneme or grapheme-to-phoneme conversion). For example, phonetic transcriptions and prosody information may provide a symbolic linguistic representation that may be provided to a synthesizer, which may then convert the symbolic linguistic representation into sound.

One skilled in the art of data processing may appreciate that there are many techniques available for converting text to speech, and that variations of these techniques may also be used, without departing from the spirit of the discussion herein.

According to an example embodiment, the audio output data may be transmitted to the audio output device 148 associated with the user 160.

Figure 2A:
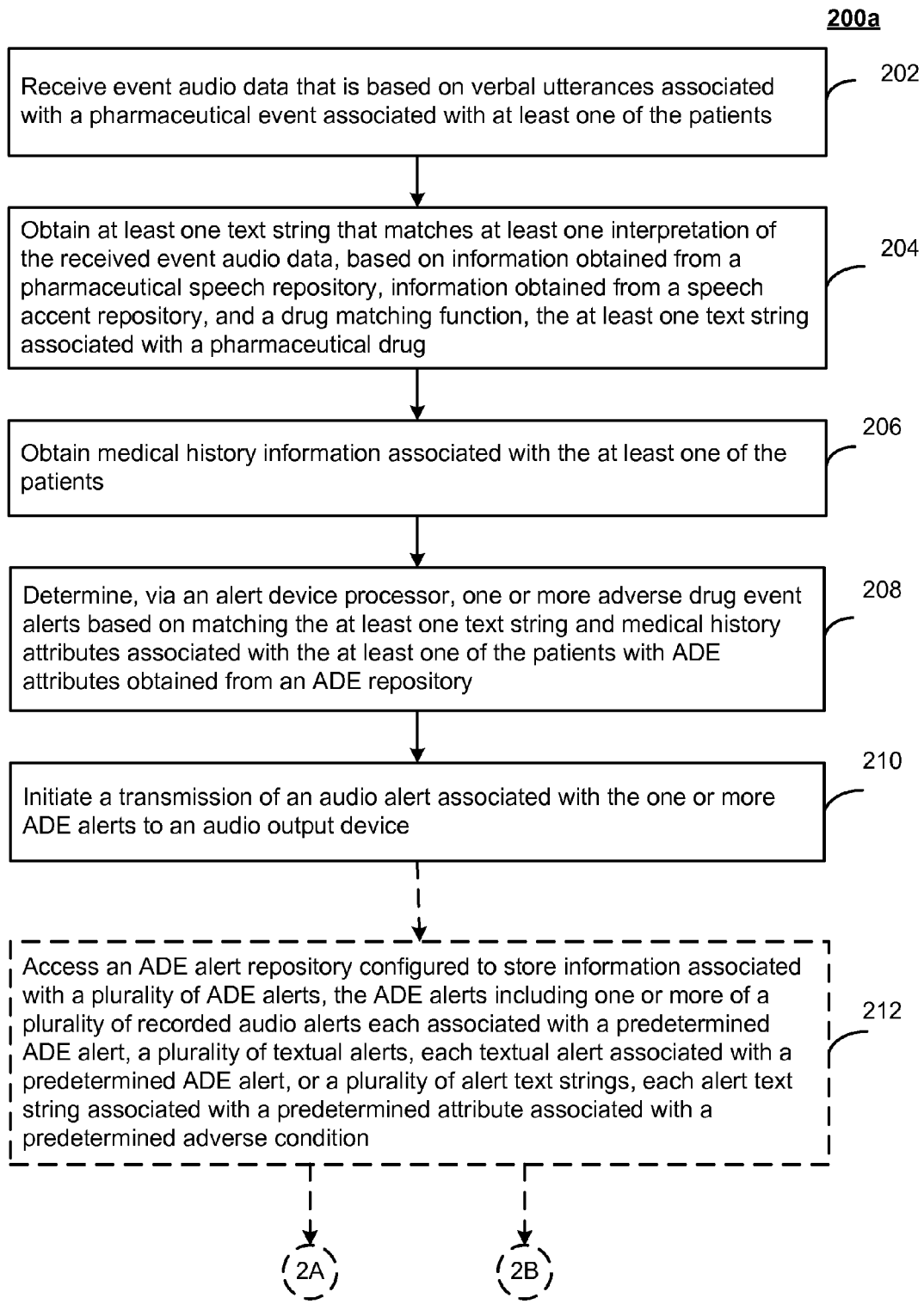
FIGS. 2a-2b are a flowchart illustrating example operations of the system of FIG. 1.
Figure 2B:
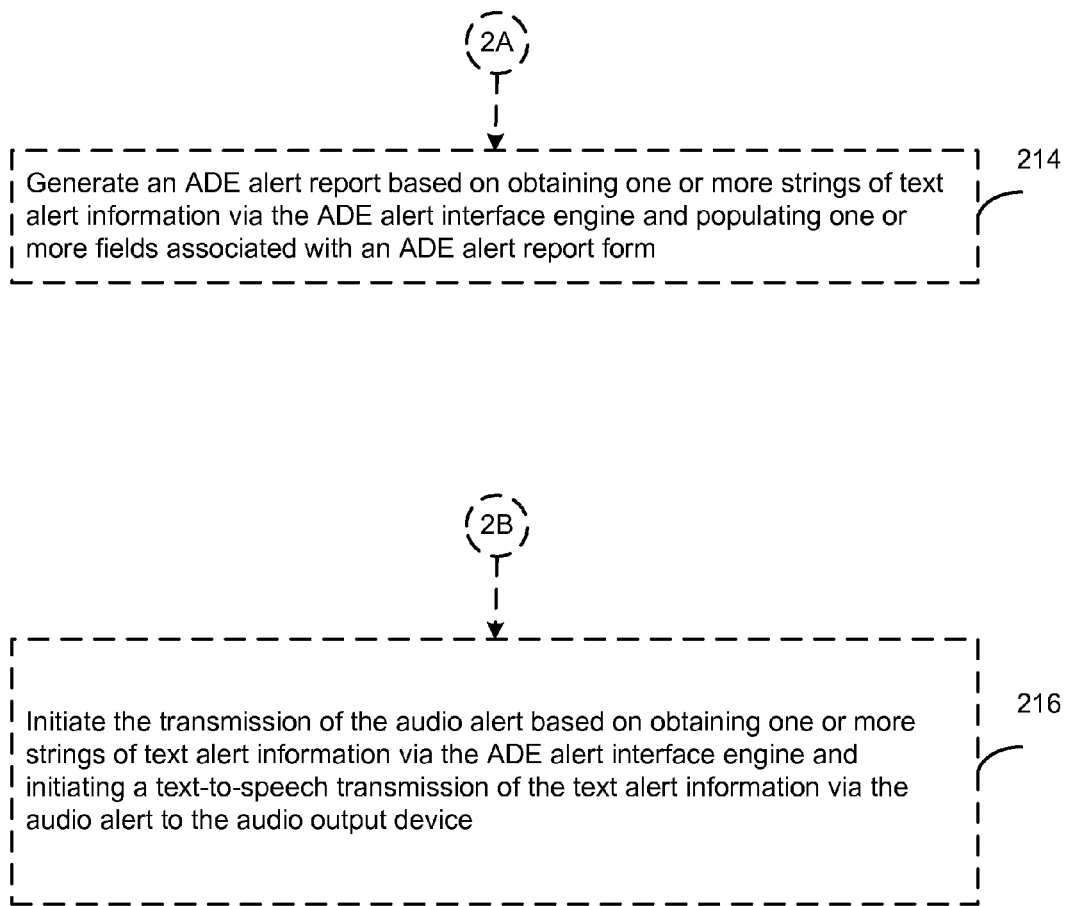

FIGS. 2a-2b are a flowchart 200 illustrating example operations of the system of FIG. 1, according to example embodiments. In the example of FIG. 2, event audio data that is based on verbal utterances associated with a pharmaceutical event associated with at least one of the patients may be received (202). For example, the audio data receiving engine 118 may receive event audio data 120 that is based on verbal utterances associated with a pharmaceutical event associated with the patient, as discussed above.

At least one text string that matches at least one interpretation of the received event audio data may be obtained, based on information obtained from a pharmaceutical speech repository, information obtained from a speech accent repository, and a drug matching function, the at least one text string associated with a pharmaceutical drug (204). For example, the recognition engine 126 as discussed above may obtain at least one text string that matches at least one interpretation of the received event audio data 120, based on information received from the pharmaceutical speech corpus interface engine 104, information received from the speech accent interface engine 108, and a drug matching function 128, the at least one text string associated with a pharmaceutical drug.

Medical history information associated with the at least one of the patients may be obtained (206). For example, the record retrieval engine 132 may obtain medical history information 116 associated with the at least one of the patients via the medical history interface engine 112, as discussed above.

One or more adverse drug event alerts may be determined, via an alert device processor, based on matching the at least one text string and medical history attributes associated with the at least one of the patients with ADE attributes obtained from an ADE repository (208). For example, the adverse drug event (ADE) scanning engine 138 may determine, via the alert device processor 140, one or more adverse drug event alerts 142 based on matching the at least one text string and medical history attributes associated with the at least one of the patients with ADE attributes obtained from the ADE interface engine 134, as discussed above.

A transmission of an audio alert associated with the one or more ADE alerts to an audio output device may be initiated (210). For example, the audio data output interface engine 144 may initiate the transmission of the audio alert 146 associated with the one or more ADE alerts 142 to the audio output device 148, as discussed above.

According to an example embodiment, the pharmaceutical event may include one or more of a medical prescription receiving event associated with the patient, or a medical prescription review event associated with the patient. According to an example embodiment, the verbal utterances may be associated with pharmaceutical personnel designated as pharmaceutical personnel responsible for pharmaceutical requests associated with the patient. For example, the pharmaceutical event may include a pharmacist/patient conference at a pharmacy counter as the patient submits a prescription form for requesting prescribed drugs from the pharmacy.

According to an example embodiment, an ADE alert repository may be accessed, the ADE alert repository configured to store information associated with a plurality of ADE alerts, the ADE alerts including one or more of a plurality of recorded audio alerts each associated with a predetermined ADE alert, a plurality of textual alerts, each textual alert associated with a predetermined ADE alert, or a plurality of alert text strings, each alert text string associated with a predetermined attribute associated with a predetermined adverse condition (212). For example, the ADE alert interface engine 150 may access the ADE alert repository 152 configured to store information associated with the plurality of ADE alerts 142, the ADE alerts 142 including one or more of a plurality of recorded audio alerts each associated with a predetermined ADE alert, a plurality of textual alerts, each textual alert associated with a predetermined ADE alert, or a plurality of alert text strings, each alert text string associated with a predetermined attribute associated with a predetermined adverse condition, as discussed above.

According to an example embodiment, an ADE alert report may be generated based on obtaining one or more strings of text alert information via the ADE alert interface engine and populating one or more fields associated with an ADE alert report form (214). For example, the ADE alert report engine 154 may generate an ADE alert report 156 based on obtaining one or more strings of text alert information via the ADE alert interface engine 150 and populating one or more fields associated with an ADE alert report form 158, as discussed above.

According to an example embodiment, transmission of the audio alert may be initiated based on obtaining one or more strings of text alert information via the ADE alert interface engine and initiating a text-to-speech transmission of the text alert information via the audio alert to the audio output device (216). For example, the audio data output interface engine 144 may initiate the transmission of the audio alert 146 based on obtaining one or more strings of text alert information via the ADE alert interface engine 150 and initiating a text-to-speech transmission of the text alert information via the audio alert 146 to the audio output device 148, as discussed above.

Figure 3A:
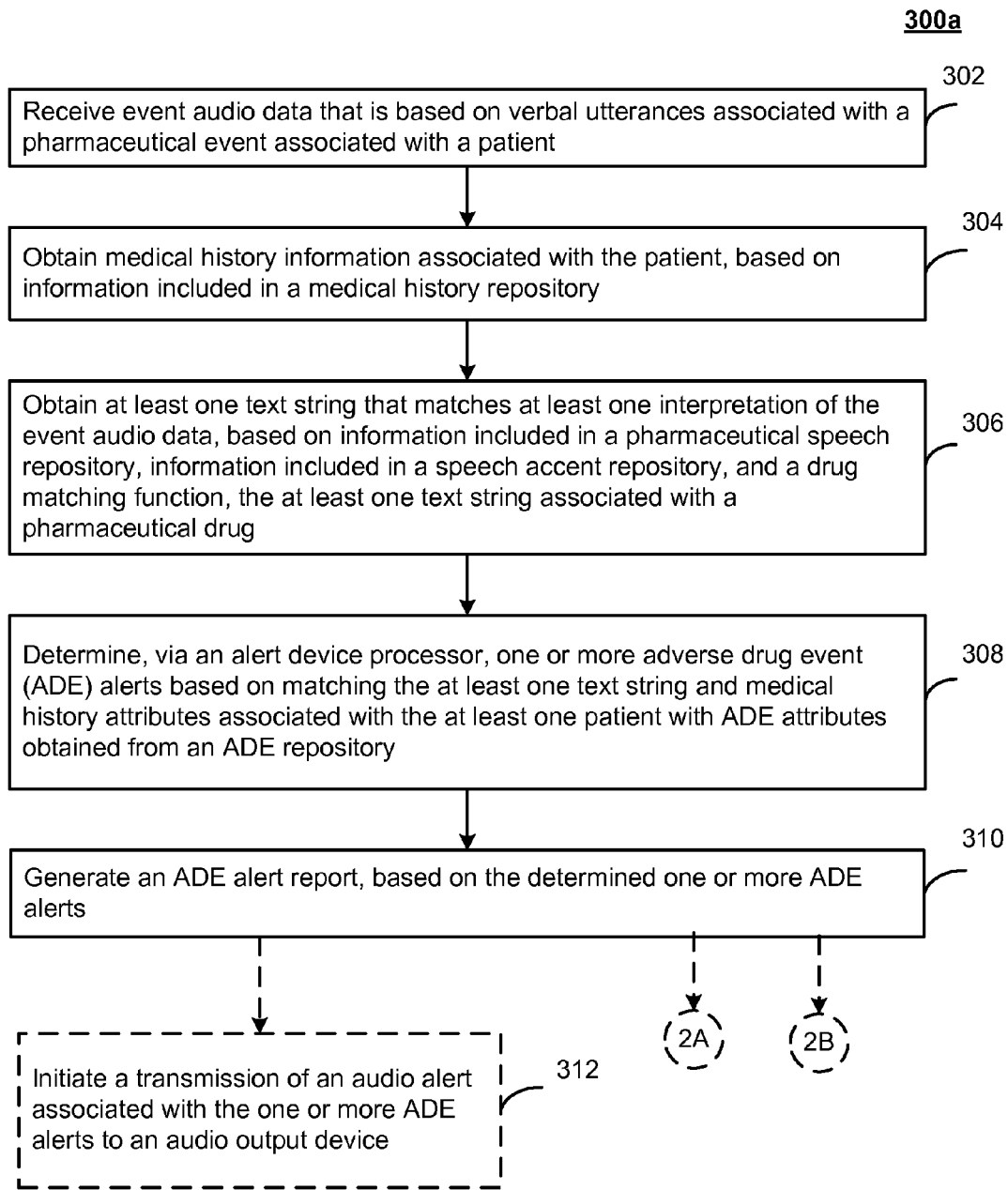
FIGS. 3a-3b are a flowchart illustrating example operations of the system of FIG. 1.
Figure 3B:
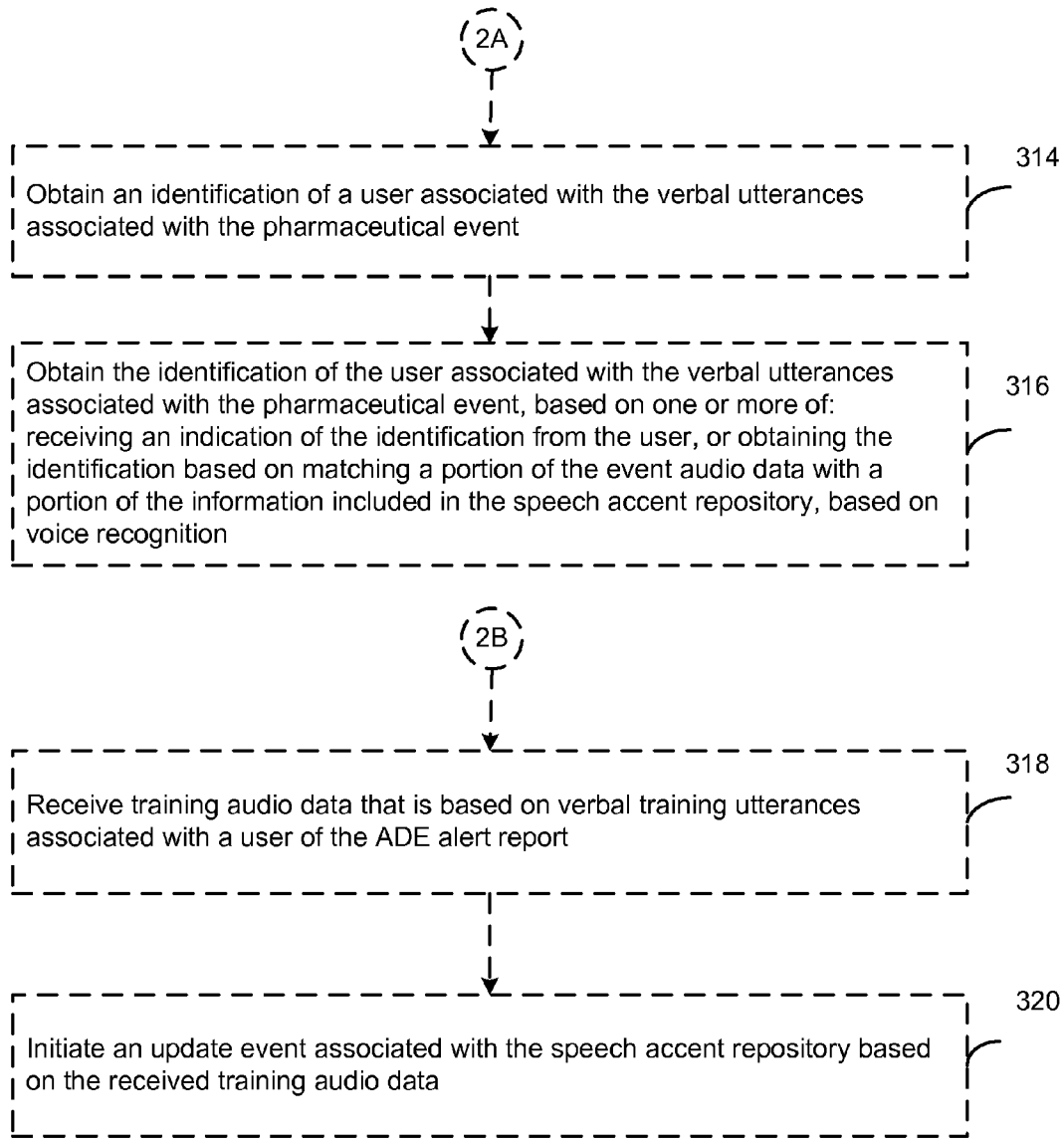

FIGS. 3a-3b are a flowchart illustrating example operations of the system of FIG. 1, according to example embodiments. In the example of FIG. 3a, event audio data that is based on verbal utterances associated with a pharmaceutical event associated with a patient may be received (302). For example, the audio data receiving engine 118 may receive event audio data 120 that is based on verbal utterances associated with a pharmaceutical event associated with the patient, as discussed above.

Medical history information associated with the patient may be obtained, based on information included in a medical history repository (304). For example, the record retrieval engine 132 may obtain medical history information 116 associated with the at least one of the patients via the medical history interface engine 112, as discussed above.

At least one text string that matches at least one interpretation of the event audio data may be obtained, based on information included in a pharmaceutical speech repository, information included in a speech accent repository, and a drug matching function, the at least one text string associated with a pharmaceutical drug (306). For example, the recognition engine 126 as discussed above may obtain at least one text string that matches at least one interpretation of the received event audio data 120, based on information received from the pharmaceutical speech corpus interface engine 104, information received from the speech accent interface engine 108, and a drug matching function 128, the at least one text string associated with a pharmaceutical drug, as discussed above.

One or more adverse drug event (ADE) alerts may be determined, via an alert device processor, based on matching the at least one text string and medical history attributes associated with the at least one patient with ADE attributes obtained from an ADE repository (308). For example, the adverse drug event (ADE) scanning engine 138 may determine, via the alert device processor 140, one or more adverse drug event alerts 142 based on matching the at least one text string and medical history attributes associated with the at least one of the patients with ADE attributes obtained from the ADE interface engine 134, as discussed above.

An ADE alert report may be generated, based on the determined one or more ADE alerts (310). For example, the ADE alert report engine 154 may generate the ADE alert report 156, as discussed above.

According to an example embodiment, a transmission of an audio alert associated with the one or more ADE alerts to an audio output device may be initiated (312). For example, the audio data output interface engine 144 may initiate the transmission of the audio alert 146 associated with the one or more ADE alerts 142 to the audio output device 148, as discussed above.

According to an example embodiment, an identification of a user associated with the verbal utterances associated with the pharmaceutical event may be obtained (314). According to an example embodiment, the identification of the user associated with the verbal utterances associated with the pharmaceutical event may be obtained based on one or more of receiving an indication of the identification from the user, or obtaining the identification based on matching a portion of the event audio data with a portion of the information included in the speech accent repository, based on voice recognition (316).

According to an example embodiment, training audio data that is based on verbal training utterances associated with a user of the ADE alert report may be received (318). According to an example embodiment, an update event associated with the speech accent repository may be initiated based on the received training audio data (320). For example, the update engine 172 may receive training audio data 174 that is based on verbal training utterances associated with the user 160, and initiate an update event associated with the speech accent repository 110 based on the received training audio data 174, as discussed above.

Figure 4A:
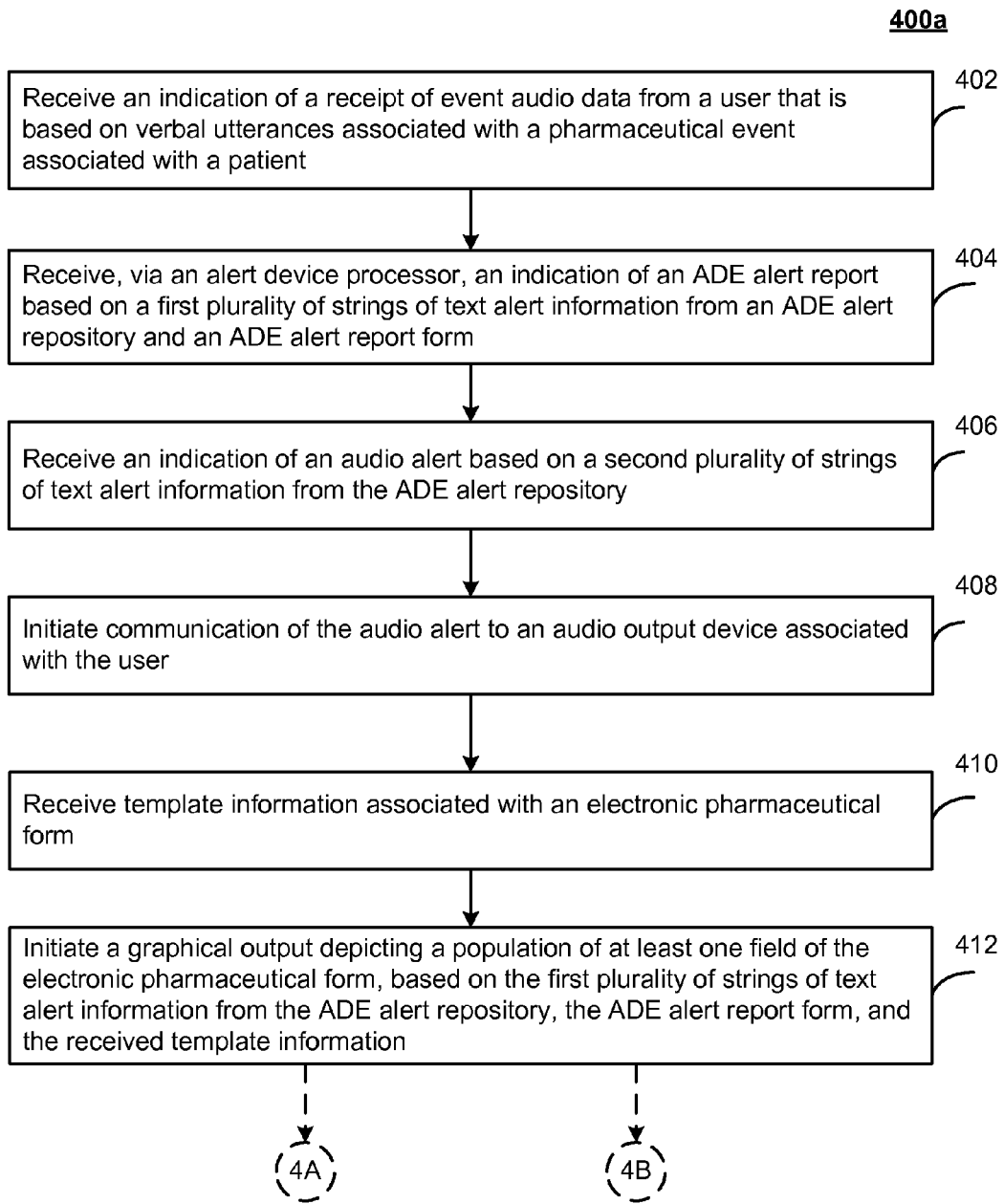

FIGS. 4a-4b are a flowchart illustrating example operations of the system of FIG. 1. In the example of FIG. 4a, an indication of a receipt of event audio data from a user that is based on verbal utterances associated with a pharmaceutical event associated with a patient may be received (402). For example, the user interface engine 162 may receive the indication of the receipt of the event audio data 114 from the user 160. According to an example embodiment, a user interface engine may also be located on a user device that may be located external to the pharmaceutical alert speech engine 102, and that may include at least a portion of the input device 124 and/or the display 131. For example, the user 160 may use a computing device such as a portable communication device or a desktop device that may include at least a portion of the input device 124 and/or the display 131, and that may be in wireless or wired communication with the pharmaceutical alert speech engine 102, and that may include the user interface engine for the user device.

An indication of an ADE alert report based on a first plurality of strings of text alert information from an ADE alert repository and an ADE alert report form may be received, via an alert device processor (404). For example, the user interface engine discussed above with regard to the user 160 computing device may receive an indication of the ADE alert report 156.

An indication of an audio alert based on a second plurality of strings of text alert information from the ADE alert repository may be received (406). For example, the user interface engine discussed above with regard to the user 160 computing device may receive an indication of the audio alert 146.

Communication of the audio alert to an audio output device associated with the user may be initiated (408). For example, the communication may be initiated as an audio communication of the audio alert 146 to the user 160 via the audio output device 148.

Template information associated with an electronic pharmaceutical form may be received (410). A graphical output depicting a population of at least one field of the electronic pharmaceutical form may be initiated, based on the first plurality of strings of text alert information from the ADE alert repository, the ADE alert report form, and the received template information (412). For example, the user interface engine discussed above with regard to the user 160 computing device may receive template information such as the template information associated with the ADE alert report form 158, and may initiate the graphical output for the user 160 via the display device 131.

According to an example embodiment, the graphical output depicting a population of at least one field of the electronic pharmaceutical form may be initiated based on one or more of initiating a graphical display of the populated electronic pharmaceutical form on a display device, based on the first plurality of strings of text alert information from the ADE alert repository, the ADE alert report form, and the received template information, initiating a graphical output to a printer, based on the first plurality of strings of text alert information from the ADE alert repository, the ADE alert report form, and the received template information, or initiating a graphical output to an electronic file, based on the first plurality of strings of text alert information from the ADE alert repository, the ADE alert report form, and the received template information (414).

According to an example embodiment, the communication of the audio alert to the audio output device associated with the user may be initiated based on one or more of initiating a text-to-speech conversion of the text alert information based on the audio alert to the audio output device associated with the user, or initiating an audio output of at least one recorded audio alert obtained from an ADE alert repository (416). For example, the user interface engine discussed above with regard to the user 160 computing device may receive the audio alert 146 as a recorded audio alert obtained from the ADE alert repository 152 and initiate communication of the recorded audio alert 146 to the audio output device 148. For example, the user interface engine discussed above with regard to the user 160 computing device may receive the text alert information and initiate a text-to-speech conversion of the text alert information to the audio output device 148 via the text-to-speech engine 178.

According to an example embodiment, an identification of a user associated with the verbal utterances associated with the pharmaceutical event may be initiated, based on one or more of a fingerprint identification of the user associated with the verbal utterances associated with the pharmaceutical event, a text entry identification of the user associated with the verbal utterances associated with the pharmaceutical event, a voice recognition identification of the user associated with the verbal utterances associated with the pharmaceutical event, or a scanned item identification of the user associated with the verbal utterances associated with the pharmaceutical event, based on a scanning of an identification item.

Figure 5:
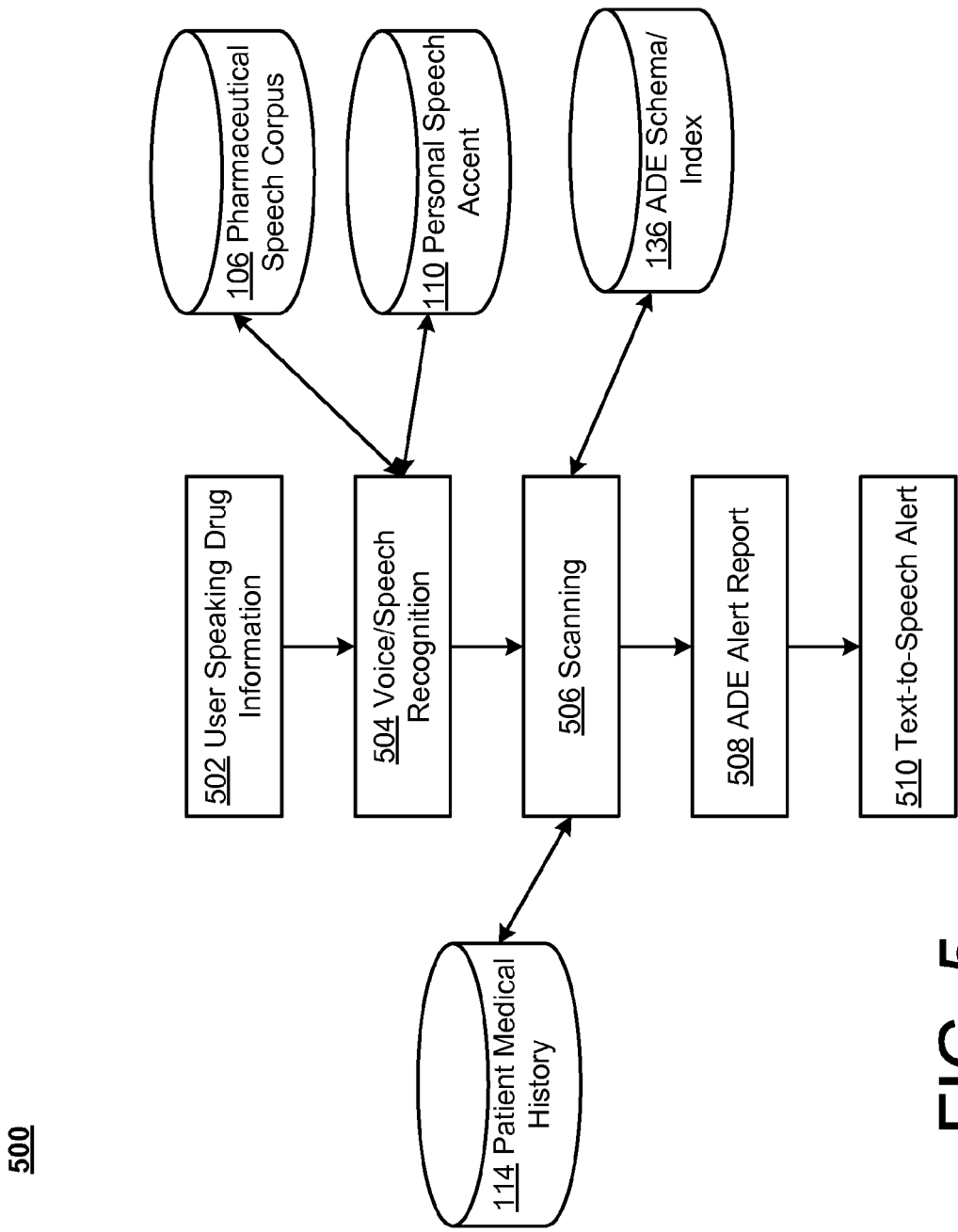
FIG. 5 is a block diagram of an example system for automated adverse drug event alerts.

FIG. 5 is a block diagram of an example system for automated adverse drug event alerts. As shown in FIG. 5, a user may speak drug information (502). For example, the user 160 may include a pharmacist or physician speaking information associated with the pharmaceutical drugs or other items into the input device 124, as discussed above. Voice/speech recognition may be performed on the spoken drug information (504). For example, the recognition engine 126 may perform the voice/speech recognition based at least on information included in the pharmaceutical speech repository 106 and the speech accent repository 110, as discussed above. For example, the recognition engine 126 may be configured to obtain the list of candidate strings 130, as discussed above.

Scanning may be performed (506). For example, the adverse drug event (ADE) scanning engine 138 may determine, via the alert device processor 140, one or more adverse drug event alerts 142 based on matching the at least one text string and medical history attributes associated with the at least one of the patients with ADE attributes obtained from the ADE interface engine 134, as discussed above.

An ADE alert report may be generated (508). For example, the ADE alert report engine 154 may generate the ADE alert report 156 based on obtaining one or more strings of text alert information via the ADE alert interface engine 150 and populating one or more fields associated with the ADE alert report form 158, as discussed above.

A text-to-speech alert may be obtained (510) and transmitted to an audio output device. For example, the audio data output interface engine 144 may initiate the transmission of the audio alert 146 based on obtaining one or more strings of text alert information via the ADE alert interface engine 150 and initiating a text-to-speech transmission of the text alert information via the audio alert 146 to the audio output device 148, as discussed above.

FIG. 6 depicts an example graphical view of a populated adverse drug event alert report. As shown in FIG. 6, a patient adverse drug event alert report 600 may be obtained as discussed above. As shown in FIG. 6, a patient name field 602 may be populated with a name of a patient. A date field 604 may be populated with a date of the report. For example, the date may be obtained from a computing system date function. A physician name field 608 may be populated with the name of an attending physician, for example, the name of a physician providing a prescription.

A patient history field 610 may be populated with medical history information 116 associated with the patient that may be obtained from the medical history repository 114. A prescription field 606 may be populated with a text indication of drug information that may have been uttered as event audio data 120 to the input device 124, as discussed above.

An alert field 612 may be populated with a text version of the ADE alert 146 that may be determined by the ADE scanning engine 138, as discussed above. A report name field 614 may indicate that the report includes a patient adverse drug event alert report 156.

According to an example embodiment, the report 600 may be displayed or printed in clear text format for later review by the patient or a caretaker of the patient, as well as for review and signature by the user 160 (e.g., before the form 600 is provided to the patient).

Patient privacy and patient confidentiality have been ongoing considerations in medical environments for many years. Thus, medical facility and pharmaceutical personnel may provide permission forms for patient review and signature before the patient's information is entered into an electronic information system, to ensure that a patient is informed of potential risks of electronically stored personal/private information such as a medical history or other personal identifying information. Further, authentication techniques may be included in order for medical facility and/or pharmaceutical facility personnel to enter or otherwise access patient information in the system 100. For example, a user identifier and password may be requested for any type of access to patient information. As another example, an authorized fingerprint or audio identification (e.g., via voice recognition) may be requested for the access. Additionally, access to networked elements of the system may be provided via secured connections (or hardwired connections), and firewalls may be provided to minimize risk of potential hacking into the system.

Further, medical and/or pharmaceutical facility personnel may provide permission forms for facility employees for review and signature before the employees' information is entered into an electronic medical information system, to ensure that employees are informed of potential risks of electronically stored personal/private information such as a medical history or other personal identifying information.

Implementations of the various techniques described herein may be implemented in digital electronic circuitry, or in computer hardware, firmware, software, or in combinations of them. Implementations may implemented as a computer program product, i.e., a computer program tangibly embodied in an information carrier, e.g., in a machine usable or machine readable storage device (e.g., a magnetic or digital medium such as a Universal Serial Bus (USB) storage device, a tape, hard disk drive, compact disk, digital video disk (DVD), etc.) or in a propagated signal, for execution by, or to control the operation of, data processing apparatus, e.g., a programmable processor, a computer, or multiple computers. A computer program, such as the computer program(s) described above, can be written in any form of programming language, including compiled or interpreted languages, and can be deployed in any form, including as a stand alone program or as a module, component, subroutine, or other unit suitable for use in a computing environment. A computer program that might implement the techniques discussed above may be deployed to be executed on one computer or on multiple computers at one site or distributed across multiple sites and interconnected by a communication network.

Method steps may be performed by one or more programmable processors executing a computer program to perform functions by operating on input data and generating output. The one or more programmable processors may execute instructions in parallel, and/or may be arranged in a distributed configuration for distributed processing. Method steps also may be performed by, and an apparatus may be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. Elements of a computer may include at least one processor for executing instructions and one or more memory devices for storing instructions and data. Generally, a computer also may include, or be operatively coupled to receive data from or transfer data to, or both, one or more mass storage devices for storing data, e.g., magnetic, magneto optical disks, or optical disks. Information carriers suitable for embodying computer program instructions and data include all forms of non volatile memory, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory may be supplemented by, or incorporated in special purpose logic circuitry.

To provide for interaction with a user, implementations may be implemented on a computer having a display device, e.g., a cathode ray tube (CRT) or liquid crystal display (LCD) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

Implementations may be implemented in a computing system that includes a back end component, e.g., as a data server, or that includes a middleware component, e.g., an application server, or that includes a front end component, e.g., a client computer having a graphical user interface or a Web browser through which a user can interact with an implementation, or any combination of such back end, middleware, or front end components. Components may be interconnected by any form or medium of digital data communication, e.g., a communication network. Examples of communication networks include a local area network (LAN) and a wide area network (WAN), e.g., the Internet.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims. While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. A system comprising:
   at least one device processor; and
   a machine readable storage device storing a pharmaceutical alert speech engine that executes on one or more of the at least one device processor, the pharmaceutical alert speech engine including:
   a medical history interface engine that accesses a medical history repository, the medical history repository storing medical history information, the medical history information being associated with a plurality of patients;
   an audio data receiving engine that receives event audio data, the event audio data being based on verbal utterances, the verbal utterances being associated with a pharmaceutical event, the pharmaceutical event being associated with at least one of the patients;
   a recognition engine that obtains at least one text string, wherein the at least one text string matches at least one interpretation of the received event audio data, wherein the obtaining the at least one text string includes transforming physical audio data into electrical data via an input device, the obtaining the at least one text string is based on information obtained from a pharmaceutical speech repository, the obtaining the at least one text string is based on information obtained from a speech accent repository, and the obtaining the at least one text string is based on a drug matching function, wherein the at least one text string is associated with a pharmaceutical drug, wherein the drug matching function includes an alternative drug matching function that determines the at least one text string, wherein the determining the at least one text string includes determining a name that is associated with an alternative drug, wherein the alternative drug is associated with the pharmaceutical drug;
   a record retrieval engine that obtains medical history information, the obtained medical history information being associated with the at least one of the patients;
   an adverse drug event (ADE) scanning engine that determines, via at least one of the at least one device processor, one or more adverse drug event alerts, the determining the one or more ADE alerts being based on results of a matching operation that compares a first set of information with ADE attributes, the determining the one or more ADE alerts including receiving the ADE attributes from an ADE repository, wherein the first set of information includes the at least one text string and includes medical history attributes which are associated with the at least one of the patients, the ADE repository being hosted on another system that is configured separately from a hosting system that hosts the medical history repository; and
   an audio data output interface engine that initiates a transmission of an audio alert to an audio output device, wherein the audio alert is associated with the one or more ADE alerts.

2. The system of claim 1, further comprising:
   a pharmaceutical speech corpus interface engine that accesses the pharmaceutical speech repository, wherein the pharmaceutical speech repository includes information which is associated with a corpus of pharmaceutical terms;
   a speech accent interface engine that accesses the speech accent repository, wherein the pharmaceutical speech repository includes information which is associated with database objects, wherein the database objects indicate speech accent attributes, the speech accent attributes being associated with one or more speakers; and
   an adverse drug event (ADE) interface engine that accesses the ADE repository, wherein the ADE repository includes attributes which are associated with adverse drug events, wherein
   the recognition engine obtains the at least one text string, wherein the at least one text string matches the at least one interpretation of the received event audio data, wherein the matching the at least one interpretation is based on information obtained from the pharmaceutical speech corpus interface engine, wherein the matching the at least one interpretation is based on information received from the speech accent interface engine, and wherein the matching the at least one interpretation is based on the drug matching function,
   the record retrieval engine obtains the medical history information, the obtained medical history information being associated with the at least one of the patients, wherein the obtained medical history information is obtained via the medical history interface engine, and
   the adverse drug event (ADE) scanning engine determines the one or more adverse drug event alerts, wherein the determining the one or more adverse drug event alerts is based on the results of the matching operation that compares the first set of information with the ADE attributes, wherein the ADE attributes are obtained via the ADE interface engine.

3. The system of claim 1 wherein the at least one text string includes one or more of:
   a name attribute associated with the pharmaceutical drug,
   a strength attribute associated with the pharmaceutical drug, or
   a dosage attribute associated with the pharmaceutical drug.

4. The system of claim 1, wherein the pharmaceutical event includes one or more of:
   a medical prescription receiving event associated with the at least one of the patients, or a medical prescription review event associated with the at least one of the patients.

5. The system of claim 1, wherein the drug matching function includes:
a user history matching function configured to determine the at least one text string, wherein the determining the at least one text string is based on a history of selected text strings, wherein the history of selected text strings is associated with a user.

6. The system of claim 1, wherein the obtained medical history information that is associated with the at least one of the patients includes one or more of:
a consumption history associated with the at least one of the patients,
an allergy history associated with the at least one of the patients,
an allergy history associated with at least one family member that is biologically related to the at least one of the patients,
a medical condition associated with the at least one of the patients, or
a medical condition associated with at least one family member that is biologically related to the at least one of the patients.

7. The system of claim 1, wherein:
the medical history repository includes a plurality of electronic medical records associated with the plurality of patients.

8. The system of claim 1, further comprising:
an ADE alert interface engine that accesses an ADE alert repository, wherein the ADE alert repository is configured to store information which is associated with a plurality of ADE alerts, the ADE alerts including one or more of:
a plurality of recorded audio alerts each associated with a predetermined ADE alert,
a plurality of textual alerts, each textual alert associated with a predetermined ADE alert, or
a plurality of alert text strings, each alert text string associated with a predetermined attribute associated with a predetermined adverse condition.

9. The system of claim 8, further comprising:
an ADE alert report engine that generates an ADE alert report, wherein the generating the ADE alert report is based on obtaining one or more strings of text alert information, wherein the one or more strings of text alert information is obtained via the ADE alert interface engine and wherein the generating the ADE alert report is based on populating one or more fields which are associated with an ADE alert report form.

10. The system of claim 8, wherein:
the audio data output interface engine is configured to initiate the transmission of the audio alert based on obtaining one or more strings of text alert information, wherein the one or more strings of text alert information is obtained via the ADE alert interface engine, and wherein the initiating the transmission of the audio alert is based on initiating a text-to-speech transmission to the audio output device, wherein the text-to-speech transmission is based on a text-to-speech transmission of the text alert information, wherein the text-to-speech transmission is accomplished via the audio alert.

11. A computer program product comprising a hardware machine readable storage device, storing executable code that, when executed, causes at least one data processing apparatus to:

receive event audio data that is based on verbal utterances, the verbal utterances being associated with a pharmaceutical event, the pharmaceutical event being associated with a patient;
obtain medical history information associated with the patient, based on information included in a medical history repository;
obtain at least one text string that matches at least one interpretation of the event audio data, the obtaining the at least one text string including transforming physical audio data into electrical data via an input device, the obtaining the at least one text string being based on information included in a pharmaceutical speech repository, the obtaining the at least one text string being based on information included in a speech accent repository, and the obtaining the at least one text string being based on a drug matching function, the at least one text string being associated with a pharmaceutical drug, wherein the drug matching function includes an alternative drug matching function that determines the at least one text string, wherein the determining the at least one text string includes determining a name that is associated with an alternative drug, wherein the alternative drug is associated with the pharmaceutical drug;
determine, via at least one device processor, one or more adverse drug event (ADE) alerts, the determining the ADE alerts being based on results of a matching operation that compares a first set of information with ADE attributes, the determining the one or more ADE alerts including receiving the ADE attributes from an ADE repository, wherein the first set of information includes the at least one text string and includes the obtained medical history information, the ADE repository being hosted on another system that is configured separately from a hosting system that hosts the medical history repository; and
generate an ADE alert report, based on the determined one or more ADE alerts.

12. The computer program product of claim 11, wherein the executable code, when executed, causes the at least one data processing apparatus to:
initiate a transmission of an audio alert associated with the one or more ADE alerts to an audio output device.

13. The computer program product of claim 11, wherein the executable code, when executed, causes the at least one data processing apparatus to:
obtain an identification of a user, wherein the user is associated with the verbal utterances.

14. The computer program product of claim 13, wherein the obtaining of the identification of the user is based on one or more of:
receiving an indication of the identification from the user, or
obtaining the identification based on matching a portion of the event audio data with a portion of the information included in the speech accent repository, wherein the matching of the portion of the event audio data is based on voice recognition.

15. The computer program product of claim 11, wherein:
the pharmaceutical event includes one or more of a medical prescription receiving event associated with the patient, or a medical prescription review event associated with the patient; and
the verbal utterances are associated with pharmaceutical personnel designated as pharmaceutical personnel who are responsible for pharmaceutical requests which are associated with the patient.

16. The computer program product of claim 11, wherein the executable code, when executed, causes the at least one data processing apparatus to:

receive training audio data that is based on verbal training utterances, wherein the verbal training utterances are associated with a user of the ADE alert report; and initiate an update event associated with the speech accent repository, wherein the update event is based on the received training audio data.

17. A method comprising:

accessing a medical history repository, the medical history repository storing medical history information, the medical history information being associated with a plurality of patients;

receiving event audio data, the event audio data being based on verbal utterances, the verbal utterances being associated with a pharmaceutical event, the pharmaceutical event being associated with at least one of the patients;

obtaining at least one text string, wherein the at least one text string matches at least one interpretation of the received event audio data, wherein the obtaining the at least one text string includes transforming physical audio data into electrical data via an input device, the obtaining the at least one text string is based on information obtained from a pharmaceutical speech repository, the obtaining the at least one text string is based on information obtained from a speech accent repository, and the obtaining the at least one text string is based on a drug matching function, wherein the at least one text string is associated with a pharmaceutical drug, wherein the drug matching function includes an alternative drug matching function that determines the at least one text string, wherein the determining the at least one text string includes determining a name that is associated with an alternative drug, wherein the alternative drug is associated with the pharmaceutical drug;

obtaining medical history information, the obtained medical history information being associated with the at least one of the patients;

determining, via at least one device processor, one or more adverse drug event (ADE) alerts, the determining the one or more ADE alerts being based on results of a matching operation that compares a first set of information with ADE attributes, the determining the one or more ADE alerts including receiving the ADE attributes from an ADE repository, wherein the first set of information includes the at least one text string and includes medical history attributes which are associated with the at least one of the patients, the ADE repository being hosted on another system that is configured separately from a hosting system that hosts the medical history repository; and initiating a transmission of an audio alert to an audio output device, wherein the audio alert is associated with the one or more ADE alerts.

18. The method of claim 17, wherein the at least one text string includes one or more of:

a name attribute associated with the pharmaceutical drug, a strength attribute associated with the pharmaceutical drug, or a dosage attribute associated with the pharmaceutical drug.

19. The method of claim 17, wherein the pharmaceutical event includes one or more of:

a medical prescription receiving event associated with the at least one of the patients, or a medical prescription review event associated with the at least one of the patients.

20. The method of claim 17, wherein the drug matching function includes:

a user history matching function configured to determine the at least one text string, wherein the determining the at least one text string is based on a history of selected text strings, wherein the history of selected text strings is associated with a user.

\* \* \* \* \*